(12) United States Patent
Pernot et al.

(10) Patent No.: US 6,600,306 B1
(45) Date of Patent: Jul. 29, 2003

(54) METHOD AND DEVICE FOR CONTROLLING A VAT CONTAINING OIL OR COOKING FAT IN SITU

(75) Inventors: Christian Pernot, Gagny (FR); Denis Le Henaff, Sevran (FR)

(73) Assignee: Metatron (FR)

( * ) Notice: Subject to any disclaimer, the term of this patent is extended or adjusted under 35 U.S.C. 154(b) by 0 days.

(21) Appl. No.: 09/937,793

(22) PCT Filed: Apr. 6, 2000

(86) PCT No.: PCT/FR00/00871
§ 371 (c)(1),
(2), (4) Date: Sep. 28, 2001

(87) PCT Pub. No.: WO00/62057
PCT Pub. Date: Oct. 19, 2000

(30) Foreign Application Priority Data

Apr. 13, 1999 (FR) .............................................. 99 04597

(51) Int. Cl.[7] .................................................. G01N 27/00
(52) U.S. Cl. ........................ 324/71.1; 324/423; 324/444
(58) Field of Search ............................ 99/330; 205/781; 324/71.1, 423, 424, 438, 439, 444, 678; 702/22

(56) References Cited

U.S. PATENT DOCUMENTS

| 5,239,258 A | 8/1993 | Kauffman .................... 205/786 |
| 5,594,327 A | 1/1997 | Sagredos et al. ........... 324/71.1 |
| 5,818,731 A | 10/1998 | Mittal et al. .................... 702/22 |
| 6,127,185 A | * 10/2000 | Melton et al. ................. 436/60 |
| 6,217,745 B1 | * 4/2001 | Fang ........................... 205/775 |
| 6,489,132 B1 | * 12/2002 | Gordon et al. ............. 435/7.92 |

FOREIGN PATENT DOCUMENTS

| DE | 30 06 696 | 10/1980 | ............. G01R/7/26 |
| FR | 82 15601 | 9/1982 | .......... G01N/33/02 |
| WO | PCT/FR00/00871 | 4/1999 | .......... G01N/33/03 |

OTHER PUBLICATIONS

Wu and Nawar Journal of the American Oil Chemists' Society, vol. 63, No. 10, A Technique for Monitoring the Quality of Used Frying Oils, Oct. 1986, p. 1363–1367.

Smith, Clifford, Hamblin and Creveling Journal of the American Oil Chemists' Society, vol. 63, No. 8, Changes in Physical and Chemical Properties of Shortenings Used for Commercial Deep–Fat Frying Aug. 1986, p.1017–1023.

Pazola, Gawecki, Buchowski, Korczak, Jankun and Grześkowiak Fette Seifen Anstrichmittel, 87 Jahrgang, No. 5, Choice of Simple Methods for Quality of Frying Fat during Deep Frying of Potato Products, 1985, p. 190–193.

Stevenson, Vaisey–Genser, and Eskin Journal of the American Oil Chemists' Society, vol. 61, No. 6 Quality Control in the Use of Deep Frying Oils, Jun. 1984, p.1102–1108.

(List continued on next page.)

Primary Examiner—N. Le
Assistant Examiner—Walter Benson
(74) Attorney, Agent, or Firm—VanOphem & VanOphem, P.C.

(57) ABSTRACT

The invention concerns a method and apparatus for monitoring the polar compound content of a liquid bath disposed within a cooking vat to insure the liquid bath remains suitable for human consumption while in use. The invention thus teaches the use of a capacitive probe configured take an initial measurement of the dielectric constant of the liquid bath and thereby define a shutdown criterion. The dielectric constant is then continuously measured during subsequent heating cycles and compared with the initial measurement. A shutdown procedure is triggered when the difference between the initial measurement and subsequent measurements reach a predetermined threshold defined by the shutdown criteria. In this manner, the polar content of the cooking vat is continuously and automatically monitored such that operator supervision is not necessary.

34 Claims, 6 Drawing Sheets

OTHER PUBLICATIONS

Kim and Maeng Korea University, Research Reports of College of Agriculture, vol. 24 Relationship between Rancidity Development and Changes of Physico–chemical Characteristics of Commercial Deep–fat Frying Oils during Thermal Oxidation, 1984, p. 101–112.

Frank, Geil and Freaso Food Technology Automatic Determination of Oxidation Stability of Oil and Fatty Products, Jun. 1982, p. 71–76.

Fritsch Journal of the American Oil Chemists' Society Measurement of Frying Fat Deterioration: A Brief Review, Mar. 1981, p. 272–274.

Fritsch, Egberb, and Magnuson Journal of the American Oil Chemists' Society, vol. 56, Changes in Dielectric Constant as a Measure of Frying Oil Deterioration Aug. 1979, p. 746–750.

Tsoukalas and Grosch Journal of the American Oil Chemists' Society, vol. 54, Analysis of Fat Deterioration—Comparison of Some Photometric Tests, Nov. 1977 p. 490–493.

* cited by examiner

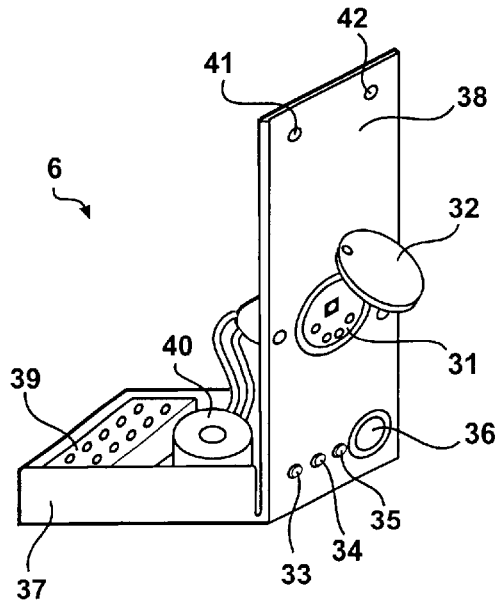
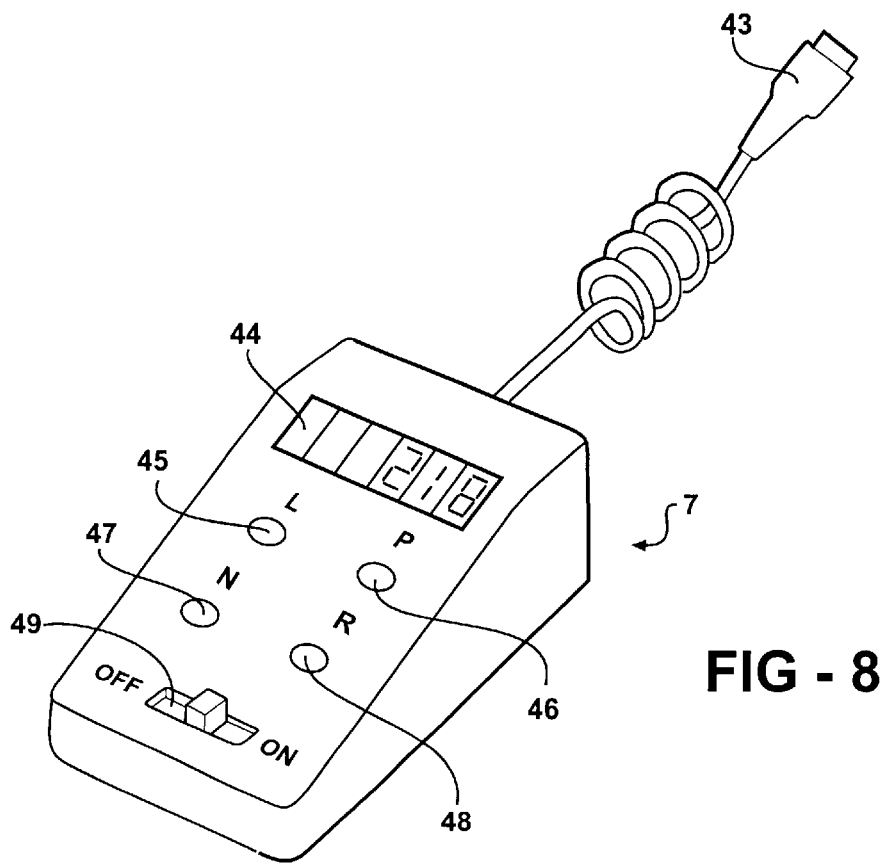

FIG - 9
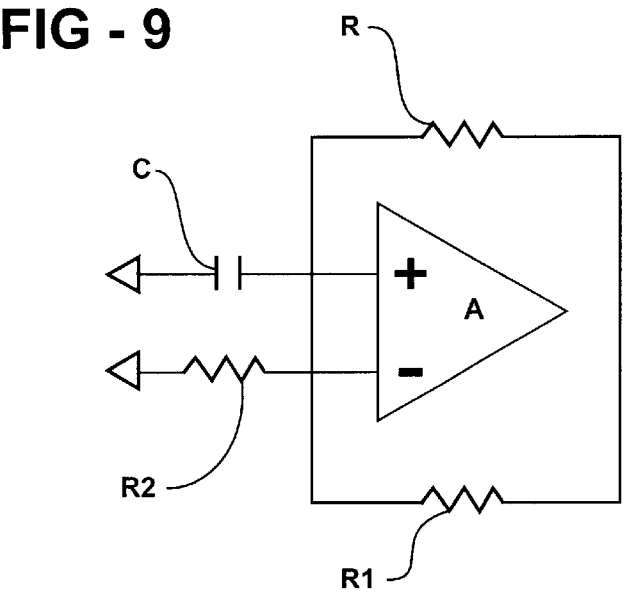
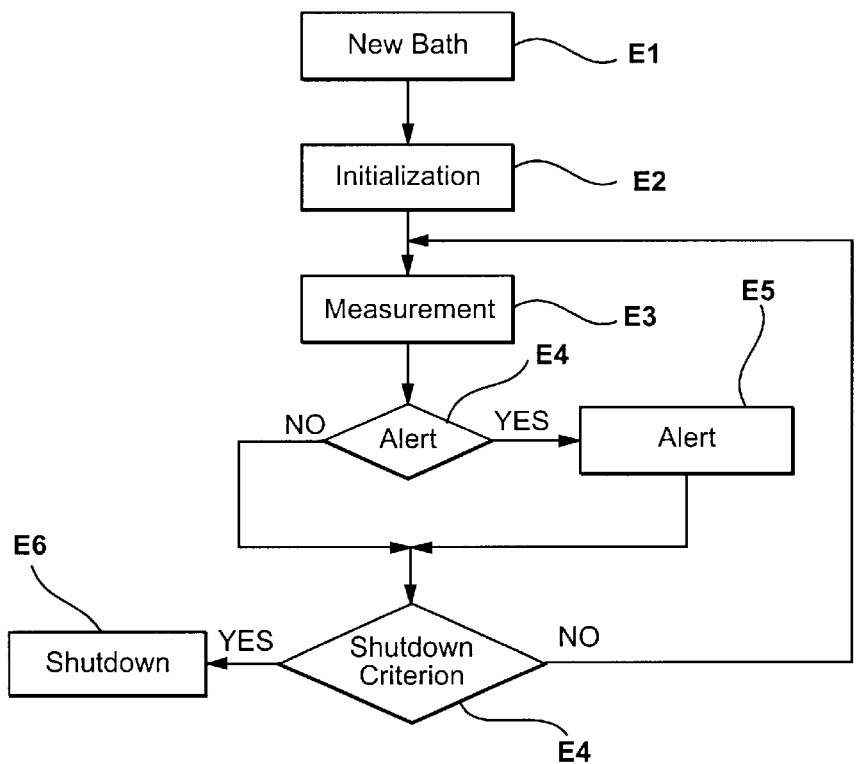
FIG - 10

METHOD AND DEVICE FOR CONTROLLING A VAT CONTAINING OIL OR COOKING FAT IN SITU

CROSS-REFERENCES TO RELATED APPLICATIONS

This application claims the benefit of International Application No. PCT/FR00/00871 filed Apr. 13, 1999.

BACKGROUND OF THE INVENTION

1. Field of the Invention

The invention relates to the in-situ monitoring of the degradation of frying oils and fats (in practice in the food sector).

2. Description of the Related Art

Food oils and fats used in cooking and frying operations undergo a thermo-oxidative alteration leading to a progressive degradation of the oil with the formation of polar compounds.

In France, decree 86–857 of Jul. 18$^{th}$, 1986 amending the decree of Mar. 11$^{th}$, 1908 stipulates that fats and oils with a polar compound content greater than 25% are unsuitable for human consumption and provides for the fixing by order of a reference analytical method for determining the polar compound content.

The current standardized reference analytical method is a liquid chromatography at atmospheric pressure followed by a solvent evaporation and a weighing (duration 3 hours). This method cannot be used for routine monitoring.

Moreover, a subjective assessment involving monitoring of the browning of the oil, the viscosity, the appearance of foam or the presence of smoke is not reliable because these criteria can appear well after the 25% limit.

More rapid methods have been developed or envisaged:

A. Methods Based on Colorimetric Reactions

"LRSM" test from 3M: this involves soaking a reactive paper in the oil. The criterion defining the end of use of an oil is the number of strips of the reactive paper that have changed color.

"OXYFRITEST" test from MERCK-CLEVENOT laboratories: a test tube is filled with oil using a syringe and some drops of reagent are added to it. After a few seconds, the color is modified according to the polar compound content. The limit of use is defined by comparison of the color obtained with a scale of reference colors.

French Patent No. FR 2 513 765 (OIL PROCESS SYSTEMS INC.) for: "Kit and process for the analysis of alkaline substances in fatty foodstuffs"; the analysis is based on a mixture of fatty material with a titration solution containing a solvent and a colorant.

B. Methods Based on the Measurement of Conductivity or Specific Resistance

U.S. Pat. No. 5,239,258 (KAUFFMAN) for: "Freshness and Stability Test Using Oxidative Degradation"; the analysis is based on the development of the current passing through a specimen relative to the voltage applied.

U.S. Pat. No. 5,594,327 (SAGREDOS et al.) for: "Method For Determining the Degree of Deterioration of Oils or Fats Used for Frying Foods"; the analysis is based on specimens introduced into a measurement cell in which, at a voltage of 100V and a temperature of 75° C., the specific ohmic resistance of the material constituting the specimen is measured.

C. Methods Based on the Measurement of the Dielectric Constant

Various scientific articles have already dealt with the problem of degradation of oils, for example:

"Changes in Dielectric Constant as a Measure of Frying Oil Deterioration", by C. W. FRITSCH et al., published in "Journal of The American Oil Chemists' Society", Vol. 56, August 1979, "Measurements of Frying Fat Deterioration. A Brief Review" by C. W. FRITSCH et al. published in JAOCS, March 1981.

These articles showed a strong correlation between the variation in the dielectric constant and the percentage of polar compounds formed. This is exploited in the German Patent Application No. DE 30 06 696 5 (NORTHERN INSTRUMENTS CORP.) providing a device for measuring dielectric properties. The device for measuring dielectric properties which is described therein is sometimes referred to by the name "Food Oil Sensor".

In practice, only the 3M and MERCK-CLEVENOT tests are used. The duration of a test is approximately one minute per deep fryer. The reliability of these tests, however, remains poor because it depends on 3 factors which are difficult to control:

1. storage conditions of the reagents: temperature, time, ambient light;
2. their use:
   the reactive papers must not be brought into contact with other objects and must be immersed for a precise time (a few seconds) in the homogenized oil; and
   it is vital that the quantity of reagent (a few drops) be observed; and
3. measurement and interpretation:
   this must be carried out after a precise period (about ten seconds) and is valid only for a fixed period (about 30 seconds); and
   the color changes are progressive and require a degree of experience in order to be read correctly.

As a general rule, all the tests available or mentioned in the literature have the disadvantage of involving sampling, i.e. the taking of samples which are analyzed outside the mass of the fatty material in use. The reliability of the monitoring therefore depends on the periodicity and regularity of the tests.

Of course, the overall reliability also depends on the reliability of the conclusions drawn from the results of the test operations.

All the methods which require prior preparation (chemical, colorimetric, or even electric, U.S. Pat. No. 5,239,258) cannot be used for in-situ monitoring and are hardly suitable for frequent monitoring (typically several times during a heating cycle).

U.S. Pat. No. 5,594,327 describes a method of measuring the variation in conductivity using a DC voltage of 100 V, a method inapplicable for monitoring in a commercial cooking vat (problem of safety voltage).

It must be noted with regard to this latter document that it mentions, among other monitoring techniques, measurement of the dielectric constant of the cooking bath, but considers this method to be complex and costly in terms of monitoring time, without stating a reason. However, the following comments can be made:

A. With Regard to Complexity

The composition of frying oils and fats is always changing, according to clients' needs and/or the purchase price of the raw materials. For example, an oil can contain animal fats (suet for example), vegetable fats (palm for example), an anti-oxidant (Exxx), and/or an anti-foaming agent (Eyyy). However, the permittivity of such an oil at 180° C. (typical usage temperature) does not appear in any publication, including the manufacturer's technical specifications, nor do its dispersion during successive production stages, or its variation when it contains 25% of polar compounds.

Moreover, each catering group uses an oil or a fat the composition of which it has determined itself.

B. With Regard to the Cost in Terms of Monitoring Time

The above-mentioned patent doubtless refers to the Food Oil Sensor which proceeds by sampling and that has clearly proven to be long and complex.

BRIEF SUMMARY OF THE INVENTION

An object of the present invention is to overcome the disadvantages of the known solutions, providing a process for monitoring that is at once reliable and repetitive, and that lends itself to automation so as to be able to guarantee in particular the consequences of the detection of too large a quantity of polar compounds.

To this end, the present invention proposes a process for monitoring a frying vat containing a bath of frying oil or fat intended to follow a plurality of heating cycles, according to which:

A. In a zone of the vat suitable for immersion in the bath, a capacitive probe is arranged, the dielectric space of which is constituted by a portion of the bath, and, after filling the vat with this bath, an initialization procedure is triggered during which an initial value of a characteristic representative of the dielectric constant of this bath in heating conditions is measured, and a shutdown criterion is fixed.

B. A measurement of this characteristic is repeatedly detected during the following heating cycles, and a shutdown procedure is triggered when it is detected that the shutdown criterion is met by this measurement.

The invention thus teaches the use of a capacitive, in practice permanent, probe in the cooking vat. The probe must therefore withstand an average temperature of 180° C. and its construction must satisfy the food and electric standards. The requirements for the probe can be expressed as follows:

high temperatures: 180° C. with a maximum of 210° C.;

suitability for food preparation; and sturdiness: daily cleanings and filterings of the vat by non-qualified personnel.

However, it appears that a capacitive probe is completely suitable for such conditions, taking into account its simplicity (two electrodes separated by a dielectric space immersed in the bath). Moreover, the act of comparison with the initial value of the characteristic in question makes the process reliable irrespective of a certain number of parameters that are difficult to control, and vary from one oil bath to another.

In large-capacity commercial deep fryers, the sensor does not need to be miniaturized. There is a dead zone in the cooking vat that can be used to fit a capacitive sensor of sufficient dimensions to guarantee its sturdiness and to characterize a substantial part of the oil bath that is representative of same.

Therefore, contrary to what might have been supposed beforehand, there are no particular difficulties with the permanent (in situ) installation of a capacitive probe in a frying vat.

The advantages of the proposed solution, compared with the devices known under the name "Food Oil Sensor" are therefore:

repetitive in-situ -monitoring of the oil in the cooking vat; and possibility of automatic monitoring without human involvement (this process is in fact easily automatable by means of closed-loop controls).

The process according to the invention can use various particularly advantageous arrangements, taken separately or in combination.

The detection of the measurements is advantageously periodic, if the instantaneous value of the characteristic is measured (or if an average of such instantaneous values is taken) at least once an hour (this is an order of magnitude corresponding to several measurements per heating cycle), it can be stated without difficulty that the monitoring is continuous, taking into account the speed of degradation of the oil baths (the length of their operational life is in fact typically more than 60 hours).

A simple procedure is to measure the characteristic by exciting an oscillating circuit of which the capacitive probe is part.

Various characteristics of the oscillating circuit can be used. In simple manner, the oscillation period is measured, i.e. the characteristic is measured by excitation of an oscillating circuit of which the capacitive probe is part, and said characteristic that is measured is the oscillation period of the oscillating circuit.

The measurement that is detected can be the average of several successive measurements which has the advantage of producing a smoothing effect.

The shutdown criterion preferably involves a comparison with the initial value of the characteristic.

The comparison of the measurement with the initial value of the characteristic that has been chosen can be carried out by establishing their ratio. However, in a particularly simple manner, the shutdown criterion is the exceeding of a set value threshold by the difference between the "instantaneous" measurement and the initial value of the characteristic. By way of a variant, this shutdown criterion can also be defined starting from an absolute variation of this measurement from the characteristic.

To allow the user to take steps in advance to replace a bath the life of which is nearly over, an alert criterion is also advantageously fixed (the latter may or may not be defined in relation to the initial value of the characteristic), and an alert procedure is triggered (it can be sound or vision only, without influencing the operation of the vat) when it is detected that this alert criterion is met.

In a preferred manner, when the shutdown criterion is fixed by the difference between the initial and instantaneous values, the alert criterion is advantageously fixed, in relation to the initial value of the characteristic, by a difference threshold which is less than the difference defining the shutdown criterion, and an alert procedure is triggered when this intermediate threshold is exceeded.

To minimize the possibly sudden character of the implementation of the process according to the invention, above all when the latter is automated, the shutdown procedure is advantageously inhibited until the heating cycle following that during which the shutdown criterion has been detected. There is therefore no difficulty in terminating the heating cycle in progress as normal, which avoids any untimely interruption to the supply of the fried products in the vat.

The shutdown procedure can include stoppage of the heating cycle following that during which the shutdown criterion has been detected, after a predetermined time (possibly zero) intended to allow the detection of the completion, or lack thereof, of bath replacement steps and the acquisition of the data required for the monitoring of this new bath.

It is easily understood that the reliability of the monitoring depends on the elimination of possible causes of ill-timed shutdowns. This is why, advantageously, account is taken only of measurements of the characteristic that are carried out when the temperature of the bath is at least equal to the threshold; it is thus that, in a preferred manner, a characteristic representative of the temperature of the bath is also detected, and the measurements of the characteristic or the monitoring of the shutdown criterion are inhibited when the temperature of the bath is lower than a minimum temperature threshold (if the measurement involves taking the average of several data acquisitions, each of these data acquisitions must be carried out at a temperature higher than the threshold).

To be able to benefit from past experience, and to be able to ensure a monitoring of the vat over a long period, including during the changing of the bath, data relating to previous baths is preferably stored.

When it is detected that, after a predetermined time after the start of a heating cycle following a heating cycle during which the shutdown criterion has been established, there has been no initialization procedure, the interruption of the heating cycle is provoked. This actually reflects a possible error in the behaviour of the user.

Any initialization procedure triggered after a predetermined period after the start of a heating cycle following a heating cycle during which the shutdown criterion has been established is inhibited. This prevents any attempt to unduly prolong the duration of the life of a bath by taking a new initialization value without changing the bath.

The initialization procedure is defined in relation to at least one of the stored initialization procedures of the previous baths, which makes use of the comments concerning the behavior of the previous baths so that they can, for example, be defined by precise measurement of the polar compound content.

The initialization procedure can advantageously be triggered only from a box independent of the vat. It is therefore possible to entrust this box only to an authorized person, and to thus clearly fix the responsibilities regarding the replacement of baths that have reached the end of their lives.

The invention also teaches a device for monitoring a frying vat containing a bath of frying oil or fat intended to follow a plurality of heating cycles such that the device is suited to the implementation of the process. The device for monitoring includes:

a capacitive probe arranged in a zone of the vat suitable for immersion in the bath;

a measurement and processing unit connected to the probe and to the electricity supply of the vat, and suitable for the measurement of values of a characteristic representative of the dielectric constant of this bath in heating conditions, and conceived so as to:
  store, in response to an initialization command, an initial value of this characteristic and a shutdown criterion; and
  detect, repeatedly during the heating cycles of the bath, a measurement of this characteristic, and to trigger a shutdown procedure when it is detected that the shutdown criterion is met by this measurement of the characteristic, and an initialization unit suitable for connection to the measurement and processing unit for transmitting an initialization command and initialization data concerning the shutdown criterion to the measurement and processing unit.

By analogy with the preceding comments concerning the process, according to preferred teachings of the invention, optionally combined:

the measurement and processing unit is conceived so as to measure the characteristic at least once an hour (i.e. several times per heating cycle);

the probe is fitted in an oscillating circuit, and the measurement and processing unit is conceived so as to measure the instantaneous value of a characteristic of this oscillating circuit;

the characteristic is the oscillation period of the oscillating circuit;

the measurement which is detected is an average of several successive measurements;

the measurement and processing unit is conceived so as to be able to detect the exceeding of a set value threshold defined by the initialization unit within the data concerning the shutdown criterion, by the difference between the measurement and the initial value of the characteristic;

the measurement and processing unit is also conceived so as to store an alert criterion (for example in relation to the initial value of the characteristic), defined by the initialization unit, and to trigger an alert procedure when it is detected that this alert criterion is met by the measurement of the characteristic;

the measurement and processing unit is conceived so as to inhibit the shutdown procedure until the heating cycle following that during which the shutdown criterion has been detected;

the shutdown procedure includes a method for stoppage, by cutting the supply to the vat, of the heating cycle which follows that during which the shutdown criterion has been detected, after a predetermined time;

this device also has a detecting element for measuring a characteristic representative of the temperature of the bath, and the measurement and processing unit is connected to this detecting element and is conceived so as to inhibit the measurements of the characteristic or the monitoring of the shutdown criterion when the temperature of the bath is lower than a minimum temperature threshold;

the measurement and processing unit is also conceived so as to store data relating to previous baths;

the measurement and processing unit is conceived so as to be able to detect that, after a predetermined time after the start of a heating cycle following a heating cycle during which the shutdown criterion has been established, there has been no transmission of an initialization command or data from the initialization unit, and to thus be able to trigger the interruption of the heating cycle by cutting the supply to the vat;

the measurement and processing unit is also conceived so as to inhibit any initialization command or data from the initialization unit, after a predetermined period after the start of a heating cycle following a heating cycle during which the shutdown criterion has been established;

the initialization unit is conceived so as to define the initialization data in relation to the initialization data and data exchanged with the measurement and processing unit for at least one of the previous baths; and the initialization unit is detachably connected to the measurement and processing unit.

In addition, to clearly separate the measurement and processing functions, and command functions (via the initialization command and the choice of initialization data), the measurement and processing unit is preferably fixed to the vat and the initialization unit is contained in a detachable box.

In the case of an electric deep fryer, the capacitive probe is preferably fixed in the vat below resistors with which the vat is fitted for the heating of the bath. This is in fact a site available for fitting the probe, one that in addition allows an easy fixing of the latter, and an easy connection to the outside.

In a particularly simple manner, the capacitive probe has two electrodes one of which is at the constant potential of the vat.

BRIEF DESCRIPTION OF THE SEVERAL VIEWS OF THE DRAWINGS

Items, characteristics and advantages of the invention emerge from the description which follows, given by way of non-limiting illustrative example, with reference to the attached diagrams in which:

FIG. 7 is a perspective view of an interface module of the monitor of FIG. 1;

FIG. 8 is a perspective view of the detachable monitoring box of FIG. 1;

FIG. 9 is the schematic diagram of an example of an oscillating circuit containing the measurement probe; and FIG. 10 is a simplified organigram of the process according to the invention.

DETAILED DESCRIPTION OF THE PREFERRED EMBODIMENT

Figure 1:
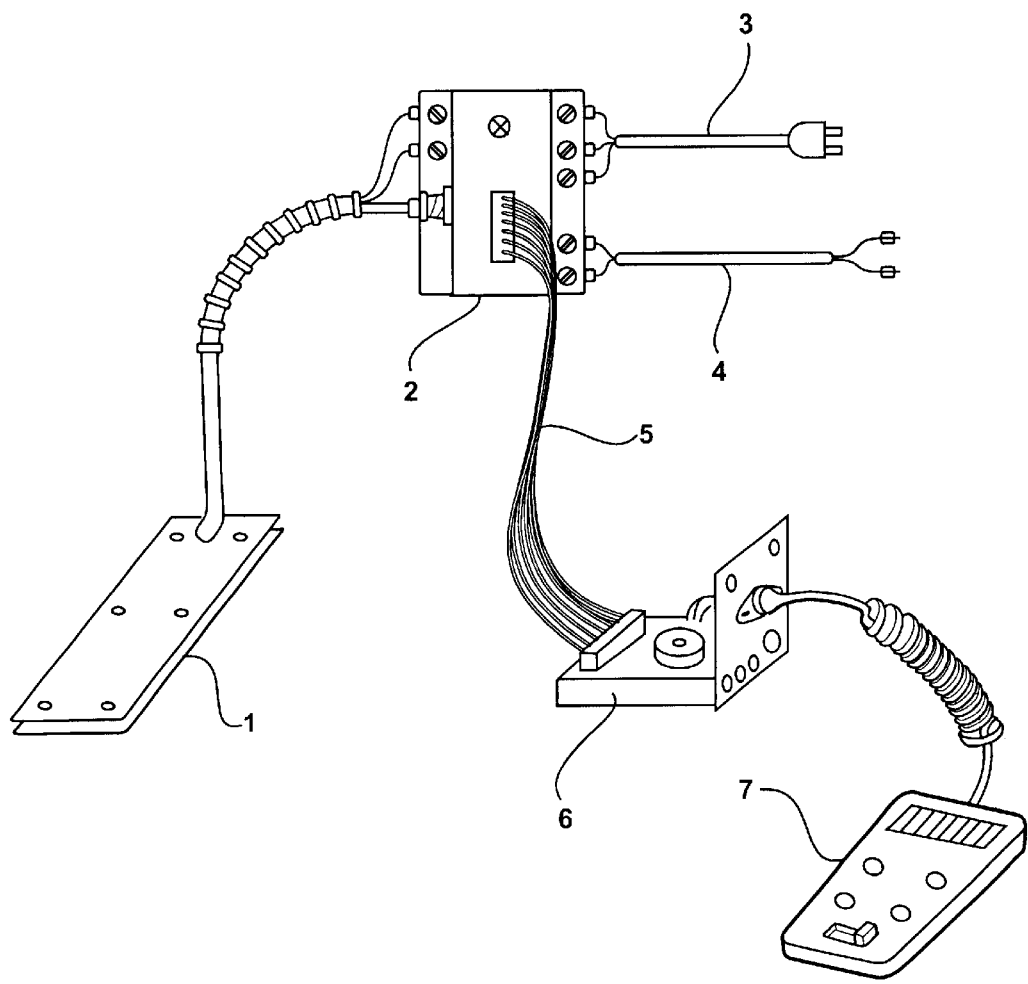
FIG. 1 is a general scheme of a monitoring device including a capacitive probe according to the invention.

FIGS. 1 to 9 represent, by way of non-limitative illustrative example, a device for monitoring a frying vat, in relation to the structure of the bath of fatty material that it contains, which contains various sub-assemblies including:

a measurement probe 1 intended to be placed in a cooking vat;

an analysis box 2 intended to be fixed beside the measurement probe 1;

an interface module 6 intended to be fixed in front of a deep fryer, on a service side, easily accessible to personnel;

a detachable box 7, connectable to the interface module 6;

a mains supply cord 3;

a cord 4 for the closed-loop control contact of the deep fryer; and a multiconductor connection cable 5 between the analysis box 2 and the interface module 6.

Figure 2:
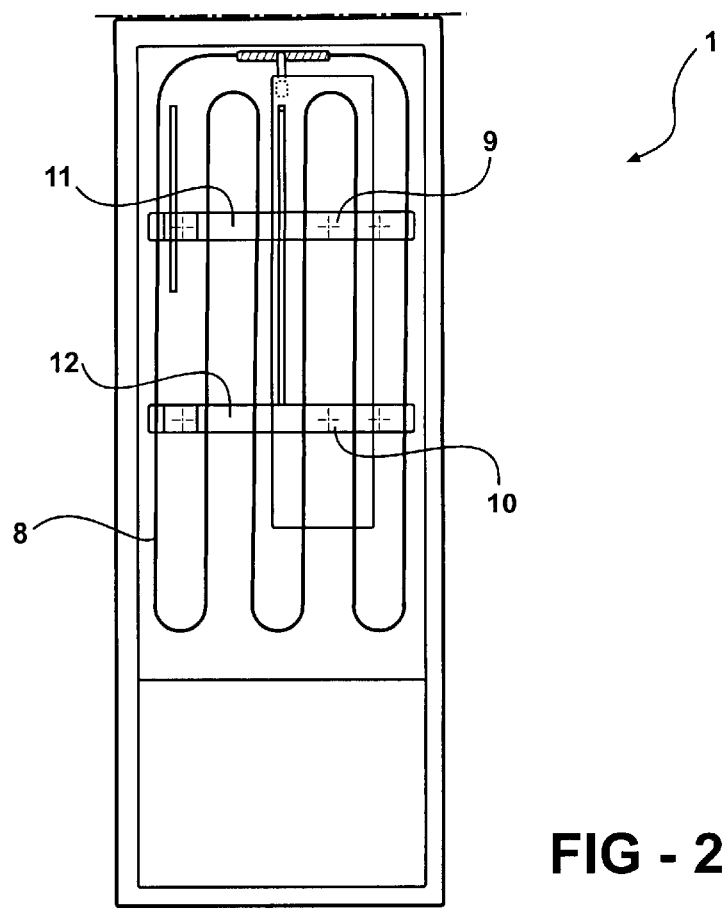
FIG. 2 is a top view of a cooking vat of an electric deep fryer in which a probe is fitted.
Figure 3:
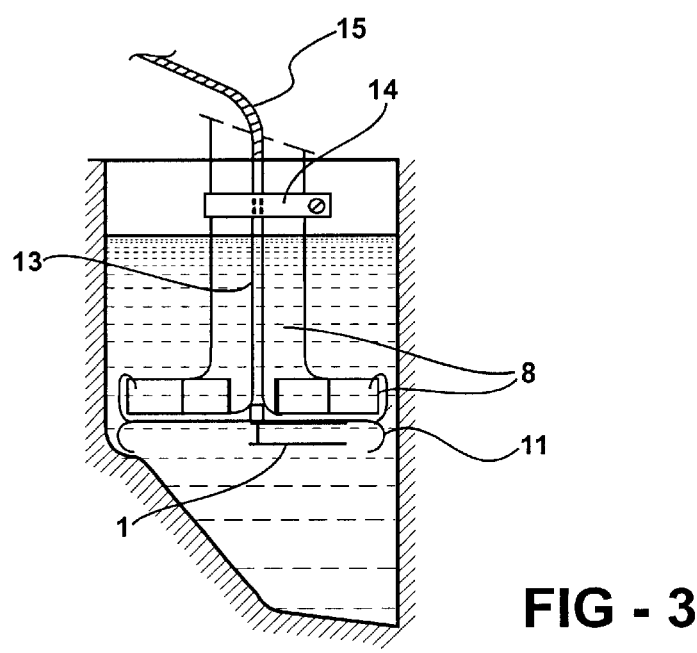
FIG. 3 is a view in vertical section.

Referring to FIGS. 2 and 3, the probe 1 is placed under a two-branch heating resistor 8 and is fixed by two nuts 9 and 10 to two bars 11 and 12 holding the resistors.

Measuring wires (not shown) are housed in a tube 13 that ascends a rear wall of the cooking vat. The tube 13 is held between the two branches of the resistor 8 by a clip 14 that provides it with mechanical protection.

A flexible stainless-steel covering 15 extends the tube 13 in order to take the measuring wires (not shown) to the analysis box 2 with the necessary protection.

Figure 4:
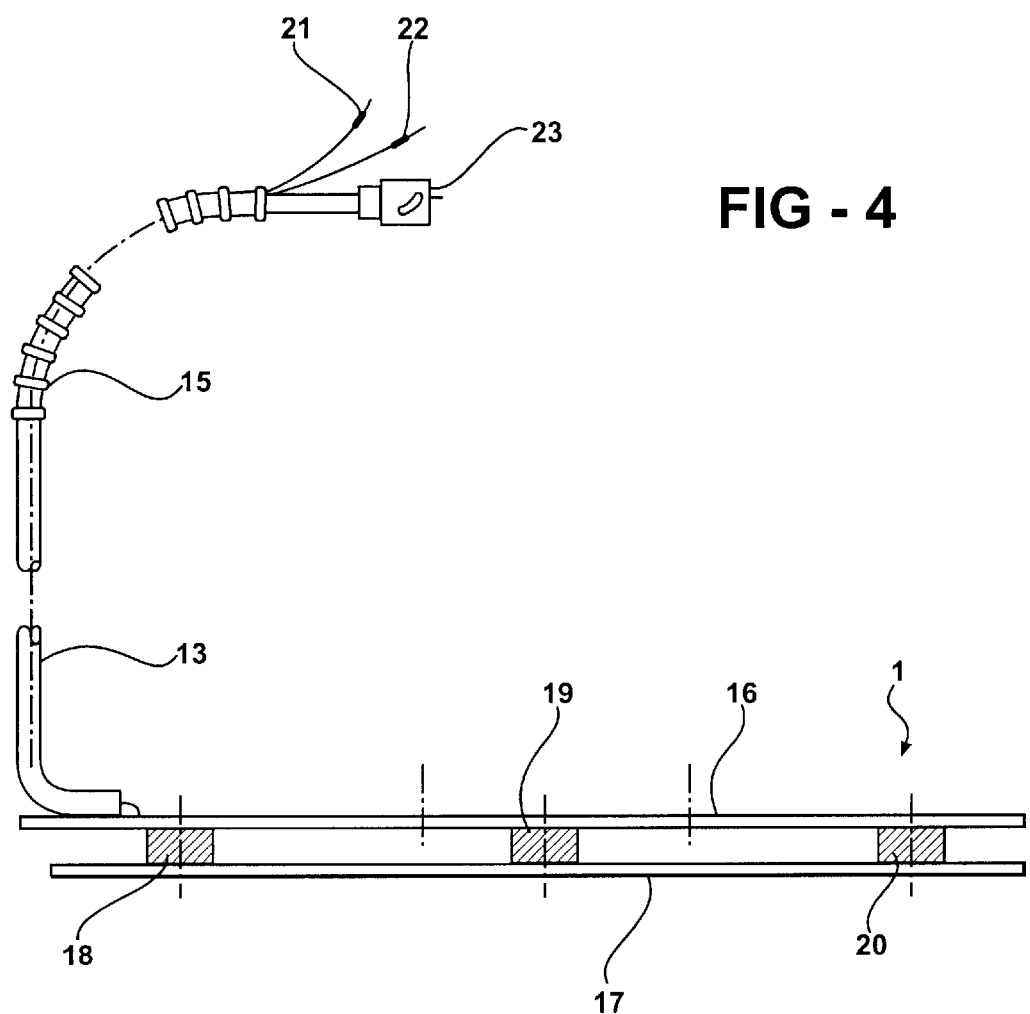
FIG. 4 is a side view of the measurement probe.
Figure 5:
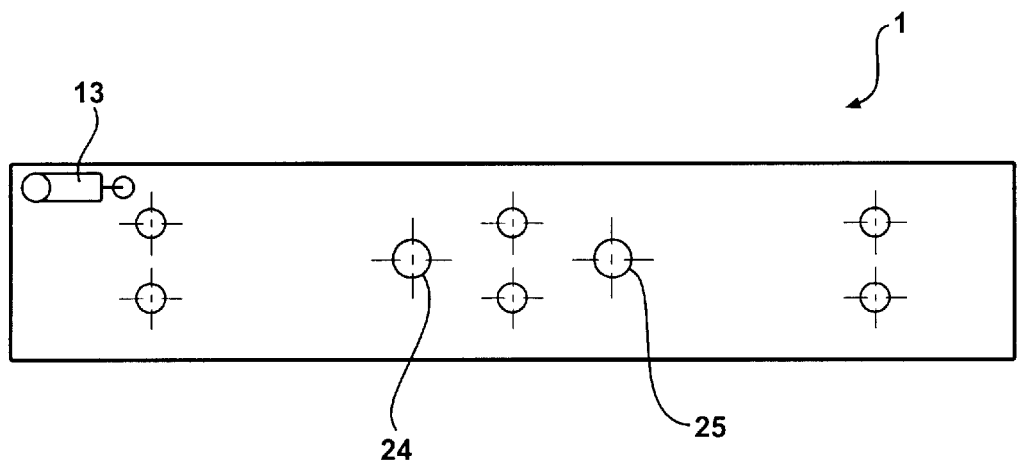
FIG. 5 is a top view of the measurement probe.

Referring to FIGS. 4 and 5, the probe 1 is preferably composed of:

an upper electrode 16, for example a 270×60 mm stainless-steel sheet 3 mm thick;

a lower electrode 17, for example a 270×60 mm stainless-steel sheet 2 mm thick;

insulators 18, 19, 20 preferably made of 8.4 mm-thick Teflon;

the tube 13, preferably stainless steel 6 mm in diameter, for protecting the measuring wires in the cooking vat;

a thermocouple having outlets 21 and 22, the active part of which is preferably at the electrode 16, inside the tube 13;

the flexible stainless-steel covering 15 protecting the measuring wires between the tube 13 and the analysis box 2;

a connector 23 linking the electrodes 16 and 17 to the analysis box 2; and tapped holes 24, 25 for fixing the probe on the bars 11 and 12.

Figure 6:
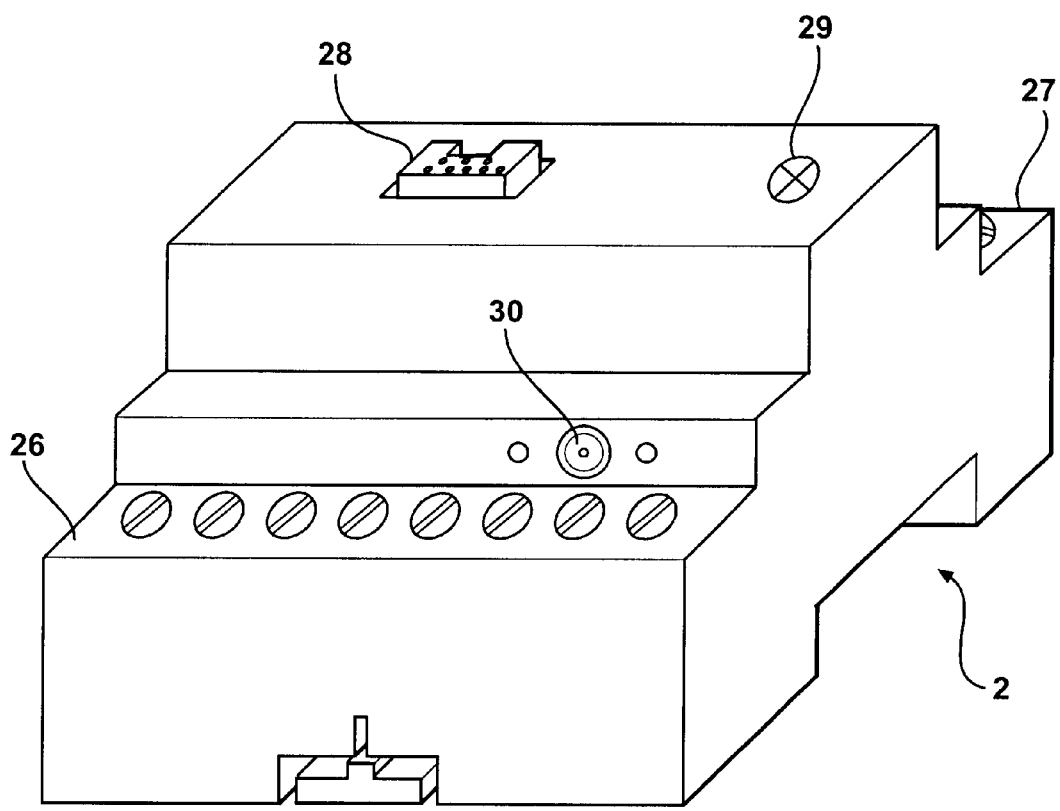
FIG. 6 is a perspective view of an analysis box of the monitor of FIG. 1.

Referring to FIG. 6, the analysis box 2 is fixed on the inside of the frame of the deep fryer (not shown), to the rear, so that the link with the measurement probe 1 is as short as possible. The analysis box 2 preferably houses:

a low-voltage supply (not shown) galvanically insulated from the sector;

a circuit (not shown) detecting the direction of connection of the sector;

a generator of periodic signals (not shown);

frequency monitoring and measurement circuits (not shown) including elements storing previous values; and a circuit measuring the temperature of the oil (not shown).

On the outside of the analysis box 2 there are advantageously fitted:

nut terminal blocks 26 and 27 for linking the thermocouple 21 and 22, the mains supply cord 3 and the closed-loop control cord 4 of the deep fryer;

a connector 28 for attaching the multi conductor connection cable 5 between the analysis box 2 and the detachable box 7;

an indicator 29 for the presence of mains voltage; and a connection base 30 for the connector 23; in an alternate embodiment, the connector 23 and the base 30 can be dispensed with if the electrodes of the measurement probe 1 are connected directly to the nut terminal blocks 26 and 27.

Referring to FIG. 7, the interface module 6 is preferably located in front of the deep fryer (not shown), behind the access door (not shown) to the equipment. It is composed here of a stainless-steel rectangle 38 to which are fitted:

a female base 31 for the link to the detachable box 7;

a pivoting guard 32 protecting the base 31;

a green indicator 33;

a yellow indicator 34;

a red indicator 35;

a pushbutton 36;

a plastic case 37 protecting the printed connection circuit (not shown);

a base 39 for connection of the multiconductor connection cable 5; and a horn or sound or other alarm 40.

The interface module is fixed to the frame (not shown) of the deep fryer (not show) by means of two holes 41 and 42.

Referring to FIG. 8, the detachable box 7 connects to the interface module 6 via a flexible cable provided with a connector 43. The detachable box 7 includes:

a 6-digit display 44;

a button L 45 for reading the memory of the analysis box 2;

a button P 46 for programming the analysis box 2;

a button N 47 for displaying different stored values;

a button R 48 for regulating the set values of the analysis box 2; and a switch 49 for switching the detachable box on or off.

The monitoring device can be analyzed as including the measurement probe 1, a measurement and processing unit (circuits for analysis of the box 2 supplemented by the elements of the module 6) and an initialization unit (detachable box 7).

In general, the process of the invention comprises the following stages, shown schematically in FIG. 10:

Stage E1: insertion of a new bath;

Stage E2: triggering of an initialization procedure during which an initial value of a characteristic representative of the dielectric constant of this bath under heating conditions is measured and a shutdown criterion is fixed as well as, optionally, an alert criterion;

Stage E3: repeated detection of a measurement of this characteristic;

Stage E4: monitoring of the shutdown criterion and optionally of the alert criterion;

Stage E5: triggering of the alert procedure when the alert criterion is detected, repeating stage E3; and Stage E6: triggering of the shutdown procedure when the shutdown criterion is detected.

The monitoring is effected in the example considered by periodically measuring the frequency (or the period) of the generator and by comparing this value with $F_{80\%}$ and $F_{used}$ frequencies calculated by the analysis box 2 at the start of the use of the considered bath from a programmed degradation set value transmitted by the detachable box 7.

The bath of oil or fat (not shown) is not homogeneous and has temperature gradients. To use the chemical tests efficiently, it is recommended, before conducting a test, to homogenize the bath by stirring it, with the help of a ladle for example, something which is in practice never done.

The frequency of the monitoring results from a compromise between the average speed of degradation of the bath and the reliability of the measurements, taking into account the above comment.

The process used by the monitor to optimize the reliability of measurements is for example as follows:

count the number of periods of the oscillator (n1) during a 5 second interval;

10 seconds afterwards; take a second count (n2) of the number of periods of the oscillator during a 5 second interval; and calculate and store from these two measurements a first average value: $M1=(n1+n2)/2$.

This sequence is repeated every 7 minutes 30 seconds.

The value taken into account to test the quality of the oil is the average of 4 successive values M1, M4 on condition that the temperature of the bath remains greater than the set temperature value during this period. In the opposite case, the. procedure is reinitialized.

The bath is thus tested regularly every half-hour. The average period of use of a bath is 72 hours (6 days) which systematically involves 144 tests compared with the 5 tests which are supposedly carried out currently.

This difference means that the monitoring can be regarded as continuous. This continuous character is all the more realistic since, if a measurement is acquired every half hour, it is the result of packets of instantaneous measurements taken every 7 minutes 30 seconds.

In principle, the procedures for acquisition of the measurements preferably involve the average of several successive measurements taken over a period sufficiently long to level out the variations due to the heterogeneous nature and to the convection movements of the bath, but sufficiently short vis-à-vis the degradation kinetics of this bath to have successive values close to each other, providing a quasi-continuity of monitoring of the state of the bath.

Upon each use of an oil of new composition, the set values to be programmed are communicated to the user, for example by the supplier. Alternatively, the user deduces the set valves from the reports from previous baths.

After detection of 100% usage, the oil must be changed and the analysis box 2 reinitialized using the detachable box 7. As this reinitialization can be carried out only by an authorized person having access to the detachable box 7, the risks of using a bath outside authorized limits are minimized. The parameterizing of the analysis boxes 2 cannot be carried out without the detachable box 7, which limits any attempt to circumvent the monitoring.

The shutdown criteria (and alert criteria, if there are any) can be defined from an absolute variation of the characteristic (the period in the example considered) but can also be defined from the initial value of this characteristic.

At the start of use of a new oil bath, the analysis box 2 must be reinitialized. This involves connecting the detachable box 7 to the interface module 6 and pressing the button P 46 twice. The indicators 33, 34 and 35 of the interface module 6 then change from flashing red to flashing green and yellow (for example for 30 minutes) and the deep fryer (not shown) is started. The monitoring really begins when only the green indicator 33 is lit, indicating that a first measurement of the initialization frequency is being carried out.

When the green and yellow indicators 33 and 34 are lit simultaneously, the monitoring is inhibited, the oil not having reached the cooking temperature (heating or temporary stoppage), typically of the order of 180° C. (a threshold of 175° C. can be fixed for example). When the red indicator 35 is permanently lit, the oil is close to the end of use (approximately 80% used), warning that a change is imminent. It is of course possible to do without this alert procedure.

The oil must be changed when the red indicator 35 flashes and when the sound alarm 40 is activated. Pressing on the pushbutton 36 stops the horn 40. The deep fryer (not shown) remains in service until it is switched off (continuity of catering service). When it is subsequently switched on, the display immediately flashes red and the horn 40 is activated. The analysis box 2 must then be reinitialized, if not, half an hour later (the time required to melt the fat and thus be able to remove it), the deep fryer (not shown) is shut down by opening the closed-loop control contact (not shown) and the horn 40 can no longer be stopped by the pushbutton 36 on the interface module 6.

As a safeguard, the 2 set values are advantageously programmable only in the half hour which follows a reinitialization (when the green and yellow indicators 33 and 34 are flashing). Any modification after this period is detected and stored. Programming the set values involves the following steps:

Set value no. 1: inhibition temperature for measurements from 0 to 254 (° C.);

Set value no. 2: period value (in principle, this is a variation) representing the degradation threshold of the oil from 0 to 255 ($\mu$s);

For this, the detachable box must be connected to the interface module then press button P 46: entry into programming mode;

press button N 47: selection of the set value (1 or 2);

press button R 48: adjustment of the value (progressive increase); and press button P 46: programming of the analysis box and exit from the mode.

To stop the monitoring in progress, the detachable box 7 must be connected and the button P 46 pressed twice, then the display changes to flashing red after 10 seconds. The deep fryer (not shown) can be reinitialized after having been switched off.

Three self diagnostic procedures are provided for ensuring the satisfactory operation of the monitor:

if the terminals of the mains supply cord 3 are not correctly connected (phase and neutral inversion), the green indicator 33 flashes, the alarm 40 is activated and the deep fryer (not shown) cannot be used (a problem which can occur when installing the monitor);

the indicators 33, 34 and 35, and the alarm 40 of the interface module 6 can be checked by pressing the pushbutton 36 only during the period of heating of the deep fryer (green and yellow indicators 33 and 34 lit); and if the measurement probe 1 has a fault, the red and yellow indicators 35 and 34 flash and the alarm 40 is activated. The stoppage procedure is the same as for detection of used oil.

The monitor (not shown) can be switched to forced working only if the measurement probe 1 has a fault in programming 255 in set value no. 1: the yellow indicator 34 lights up, the deep fryer (not shown) is switched on again but without monitoring of the oil.

To exit this mode, the detachable box 7 must be connected and the button P 46 pressed twice. The display then changes to green then 10 seconds later:

if the measurement probe 1 has been repaired, to flashing red. The detachable box 7 must then be reinitialized; and if the measurement probe 1 still shows a fault, continued probe fault display.

When the detachable box 7 is connected to the interface module 6, it firstly displays the frequency of the generator allowing a rapid assessment of the satisfactory operation of the measurement Probe 1. The used-oil temperature eight-bit byte is coded according to the type of monitoring stoppage.

detection of used oil=temperature of the bath at that moment stoppage in progress=255 (voluntary stoppage)

electrodes cut-out=254 (probe fault)

electrodes short-circuit=253 (probe fault)

thermocouple cut-out=252 (probe fault)

max. days exceeded=251 (safeguard for the maximum duration of use of the same bath)

These values can be displayed by the detachable box 7 (shown in FIG. 8).

By pressing the button L 45 of the detachable box 7 connected to the interface module 6, the information stored by the analysis box 2 is transferred into the detachable box 7 and can be examined by the latter:

1) Displaying the parameters of the bath during use.

Successive pressing of the button N 47 allows 8 values to be displayed:

no. 1 12=bath in progress;

no. 2 programmed set temperature value;

no. 3 programmed set degradation value;

no. 4 initial temperature;

no. 5 initial frequency;

no. 6 last value of the temperature measurement or coding of the type of monitoring stoppage;

no. 7 $F_{used}$ detection frequency; and (last value of the frequency measurement)

no. 8 number of days of use of the bath.

2) Display of the parameters of the last 11 previous baths.

Pressing button R 48 resets the display to parameter no. 1 of the preceding bath. The 8 parameters of this bath are accessible by pressing the button N 47 as previously indicated.

3) Display of the set values, the detection thresholds and the internal status of the monitor.

Pressing the button P 46 followed by pressing the button N 47 allows access to the following 8 values:

no. 1 set temperature value (adjustable between 0 and 254);

no. 2 set degradation value (adjustable between 0 and 255);

no. 3 initial frequency of the bath in progress;

no. 4 $F_{used}$ frequency of the bath in progress calculated by the analysis box 2;

no. 5 $F_{80\%}$ frequency of the bath in progress calculated by the analysis box 2;

no. 6 internal status of the analysis box 2;

no. 7 number of measurements taken since reinitialization; and no. 8 storage address in progress.

The device described above is very comprehensive and combines several essential and supplementary characteristics of a device according to the invention (which can thus be simpler). However, in this regard, the following advantages can be noted:

A) a permanent monitoring of the oil or the fat:

the measurement probe 1 is placed permanently in the cooking vat, and the analysis, closed-loop control and signalling device is fixed to the interior of the deep fryer;

B) an automatic monitoring:

after reinitialization of the monitoring device when filling the cooking vat with new oil, the monitoring of the degradation does not require any human action;

C) a monitoring which inhibits, after a delay, the use of the deep fryer with a used oil or fat:

thanks to a contact available on the analysis box, 2, wired in series with the supply of the command system (not shown) of the deep fryer (not shown) and which opens 30 minutes after the deep fryer has been switched on again, a detection having taken place before the last switching-off of the deep fryer, and the reinitialization of the monitor not having been carried out in this period of time;

D) a monitoring using a capacitive probe:
the measurement probe 1 is mainly constituted by 2 metal electrodes 16 and 17 insulated from each other to form a capacitor in which the oil or the fat to be monitored fills the inter-electrode space and constitutes the dielectric of the capacitor;

E) a monitoring where the capacitive probe is for example part of an oscillator according to the schematic diagram in FIG. 9:
its oscillation period T=aC where a is a constant fixed by the values of these resistors R, R1 and R2 and where C is a capacity composed of the sum of two capacities:
1) a capacity $C_f$, fixed for the monitor but capable of varying from one monitor to another, itself the sum of 2 capacities:
   a) the input capacitance of the operational amplifier; and
   b) the capacity of the connection cable between the monitor and the probe.
2) a capacity $C_s$ which is the capacity of the measurement probe. It is equal to $\in_r \times C_{s\text{-}air}$ where $\in_r$ is the relative permittivity of the oil and $C_{s\text{-}air}$ the capacity of the probe measured under vacuum or in the air;

F) a monitoring where one electrode of the measurement probe 1 is at the potential of the cooking vat:
the oscillator (not shown) used allows the vat to be used as one of the electrodes of the measurement probe 1 to simplify its design and reduce its cost;

G) a monitoring based on the measurement of the absolute variation $\Delta T$ in the period T of the oscillator (not shown):
the period $T = a \cdot (C_f + C_s)$; and
the relative permittivity of the new oil or the fat is graded $\in_m$ and that of the used oil or fat graded $\in_{ru}$ with $\in_{ru} > \in_m$. The variation $\Delta T$ in the period T of the oscillator (not shown) between a new oil or a fat and a used oil or fat is:
$T = T_u - T_n$, i.e. $\Delta T = a \times C_s \times (\in_{ru} - \in_m)$; and
$\Delta T$ does not depend on the capacity of $C_f$. This leads to an excellent interchangeability between probes and monitors.

H) a monitoring the detection thresholds of which are calculated from $\Delta T$:
after reinitialization during an oil change, the analysis box 2 determines the frequency $f_i$ to be taken into account for the initialization. It calculates from this frequency and from the set value $\Delta T$ the period $T_{80\%}$ corresponding to an 80% degradation and the period $T_{used}$ corresponding to a used oil, and deduces from this the frequencies $F_{80\%}$ and $F_{used}$ which are the 2 detection thresholds of the monitoring;

I) a monitoring the set value $\Delta T$ of which is fixed experimentally by comparative trials with the standardized reference analysis method:
$\Delta T$ is an absolute value which depends only on the geometric characteristics of the measurement probe, the constant a of the generator (not shown) and the permittivity of the oil or fat to be monitored.

J) a monitoring the frequency $f_1$ of which taken into account in the initialization for calculating the set values is the maximum frequency measured during the first hours of use of the bath of oil or fat;

K) a monitoring the frequency of the oscillator (not shown) of which is such that, for the minimum variation $\Delta T$ to be detected, the variation in corresponding frequency is close to (100/p) in Hz where p represents the % precision of measurement;

L) a monitoring where a temperature sensor (not shown) is incorporated into the measurement Probe 1;

M) a monitoring the set temperature value of which allows measurement to be inhibited when the temperature of the oil or fat is lower than the set value;

N) a monitoring the set values of which are only programmable with an external box;

O) a monitoring the programming of the set values of which is possible only during the half-hour which follows a change of oil, an arrangement which prevents any modification of these during the use of a bath;

P) a monitoring where the switching back on of the deep fryer (not shown) after opening of the closed-loop control contact of the analysis box 21 shown in FIG. 6 is possible only with an external box;

Q) a fixing of the measurement probe 1 where the electrodes are vertical, to reduce their clogging;

R) the fitting of the oscillator (not shown) very close to the measurement probe 1:
an arrangement which allows the maximum detection possibilities to be obtained with economic analysis electronics;

S) a self-diagnosis which tells the user of any fault in the measurement probe 1 or in the temperature sensor (not shown); and T) a separate interface module 6 having the three indicators 33, 34 and 35 required to show the degree of use of the oil or fat and for monitoring the measurement probe 1 and the temperature sensor (not shown), the alarm 40 the multiconductor connection cable 51 to the detachable box 7, the pushbutton 36 used to test or stop the alarm 40 and displays test which allows easy installation in the deep fryer (not shown), at a suitable place, in a restricted space.

It can be observed that the device according to the invention has a very moderate consumption. Even when the oscillator (not shown) is permanently excited, the monitor typically has a consumption of the order of 2 W, which is very low compared with the installed power (usually of the order of 20 kW). It is therefore not necessary (although possible) to provide for phases of consumption reduction.

The above description has only an indicative, non-limitative character, numerous variants can be proposed without exceeding the scope of the invention.

What is claimed is:

1. A process for monitoring a heating vat comprising:
obtaining a liquid bath disposed within said heating vat, said liquid bath being exposed to a plurality of heating cycles and having a predetermined dielectric constant;
arranging a capacitive probe having a dielectric space in said heating vat whereby said capacitive probe is immersed in said liquid bath such that said dielectric space is constituted by a portion of said liquid bath;
providing an initialization procedure comprising the following steps:
measuring an initial value of a characteristic representative of said dielectric constant of said liquid bath; and establishing a shutdown criterion based on said initial measurement of said characteristic representative of said dielectric constant of said liquid bath;

triggering said initialization procedure;

measuring said characteristic repeatedly during said plurality of heating cycles;

monitoring said shutdown criterion during said plurality of heating cycles;

defining a shutdown procedure whereby said shutdown procedure automatically interrupts said plurality of heating cycles after a predetermined time such that said liquid bath can be replaced; and triggering said shutdown procedure when said shutdown criterion is met.

2. The process according to claim 1 further comprising the step of measuring an instantaneous value of said characteristic at least once an hour during operation of said process.

3. The process according to claim 2, wherein said measuring said instantaneous value of said characteristic further comprises averaging a plurality of instantaneous measurements.

4. The process according to claim 3, wherein said measuring said instantaneous value of said characteristic further comprises exciting an oscillating circuit having an oscillation period that defines said characteristic.

5. The process according to claim 4, wherein said shutdown criterion is defined in relation to said initial value of said characteristic.

6. The process according to claim 5 further comprising the steps of establishing a set value threshold; and determining a difference between said instantaneous value of said characteristic and said initial value of said characteristic, whereby said shutdown criterion is established when said difference between said instantaneous value of said characteristic and said initial value of said characteristic exceeds said set value threshold.

7. The process according to claim 5 further comprising the steps of establishing an alert criterion; establishing an alert procedure; and initiating said alert procedure when said alert criterion is satisfied.

8. The process according to claim 7, wherein said alert criterion is also fixed in relation to said initial value of said characteristic, defined by an intermediate threshold of the difference between said initial and said instantaneous values of said characteristic which is less than the difference defining said shutdown criterion, and further wherein said alert procedure is triggered (E5) when said intermediate threshold is exceeded.

9. The process according to claim 8 further comprising the step of inhibiting said shutdown procedure until a heating cycle following that during which said shutdown criterion has been detected.

10. The process according to claim 9, wherein said shutdown procedure further comprises the step of stopping a heating cycle following that during which said shutdown criterion has been detected, after a predetermined time.

11. The process according to claim 10 further comprising the steps of detecting a characteristic representative of the temperature of said liquid bath; establishing a minimum temperature threshold; and inhibiting said measuring of said instantaneous value of said characteristic, and said monitoring of said shutdown criterion when said characteristic representative of said temperature of said liquid bath is less than said minimum temperature threshold.

12. The process according to claim 11 further comprising the steps of replacing said liquid bath disposed within said heating vat with a new liquid bath periodically, thereby defining at least one previous liquid baths; establishing data relating to each said liquid bath; and recording said data relating to each of said at least one previous liquid baths.

13. The process according to claim 12 further comprising the step of interrupting one of said plurality of heating cycles within a predetermined amount of time following detection of said shutdown criterion if said initialization procedure has not been triggered.

14. The process according to claim 12 further comprising the step of inhibiting an initialization procedure triggered after a predetermined period after the start of a heating cycle following a heating cycle during which said shutdown criterion has been established.

15. The process according to claim 14, further comprising the steps of recording at least one previous initialization procedure relating to said at least one previous liquid baths; and defining said initialization procedure in relation to said at least one previous initialization.

16. The process according to claim 15, further comprising the step of providing a box independent of said heating vat, whereby said initialization procedure can be triggered only from said box.

17. A device for monitoring a heating vat comprising:

a heating vat comprising a power source;

a liquid bath disposed within said heating vat, said liquid bath having a dielectric constant;

means for creating a plurality of heating cycles within said liquid bath;

a capacitive probe arranged in a zone of said heating vat for immersion in said liquid bath;

a measurement and processing unit connected to said capacitive probe and to said power source of said heating vat, said measurement and processing unit comprising:

means for measuring an initial value of a characteristic representative of said dielectric constant of said liquid bath during said plurality of heating cycles;

means for defining a shutdown criterion in relation to said initial value of said characteristic;

means for monitoring said shutdown criterion during said plurality of heating cycles;

means for storing said initial value of said characteristic representative of said dielectric constant and said shutdown criterion in response to an initialization command;

means for measuring said characteristic representative of said dielectric constant periodically during said plurality of heating cycles of said liquid bath;

means for defining a shutdown procedure comprising automatically interrupting said plurality of heating cycles after a predetermined time such that said liquid bath can be replaced; and means for triggering said shutdown procedure when said shutdown criterion is met; and an initialization unit connected to said measurement and processing unit, said initialization unit comprising:

means for receiving said initialization command, and transmitting said initialization command to said measurement and processing unit; and means for receiving initialization data concerning said shutdown criterion, and transmitting said initialization data to said measurement and processing unit.

18. The device according to claim 17, wherein said means for measuring said characteristic of said measurement and processing unit is configured to measure said characteristic at least once an hour.

19. The device according to claim 18, wherein said means for measuring said characteristic of said measurement and processing unit is configured to establish said measurement of said characteristic based on a plurality of successive instantaneous measurements spread over a period separating consecutive measurement detections.

20. The device according to claim 19 further comprising an oscillating circuit fitted to said probe, whereby a characteristic of said oscillating circuit is measured by said measurement and processing unit.

21. The device according to claim 20, wherein said characteristic comprises an oscillation period of said oscillating circuit.

22. The device according to claim 21, wherein said initialization unit comprises means for defining a set threshold value, and further wherein said measurement and processing unit comprises:

means for calculating a difference between said detected measurement and said initial value of said characteristic; and means for detecting when said difference between said detected measurement and said initial value of said characteristic exceeds said set value threshold.

23. The device according to claim 22, wherein said initialization unit comprises means for defining an alert criterion, and further wherein said measurement and processing unit comprises:

means for storing said alert criterion; and means for triggering an alert procedure when it is detected that said alert criterion is satisfied by the detected measurement of the characteristic.

24. The device according to claim 23, wherein said measurement and processing unit comprises means for inhibiting said shutdown procedure until a heating cycle following that during which said shutdown criterion has been detected.

25. The device according to claim 24 further comprising means for cutting off said power source of said heating vat after a predetermined amount of time following detection of said shutdown criterion.

26. The device according to claim 25 further comprising a detection element connected to said measurement and processing unit for measuring a characteristic representative of the temperature of the bath, and further wherein said measurement and processing unit comprises:

means for establishing a minimum temperature threshold; and means to inhibit said measuring of said characteristic or said monitoring of said shutdown criterion when the temperature of said liquid bath is lower than said minimum temperature threshold.

27. The device according to claim 26, wherein said liquid bath is periodically replaced with a new liquid bath, thereby defining at least one previous liquid bath, and further wherein said measurement and processing unit is configured to store data relating to said at least one previous liquid bath.

28. The device according to claim 27, characterized in that the measurement and processing unit is conceived so as to be able to detect that, after a predetermined time after the start of a heating cycle following a heating cycle during which the shutdown criterion has been established, there has been no transmission of an initialization command or of data from the initialization unit, and to be able to then trigger the interruption of the heating cycle by cutting the supply to the vat.

29. The device according to claim 28, characterized in that the measurement and processing unit is also conceived so as to inhibit any command or initialization data from the initialization unit, after a predetermined period after the start of a heating cycle following a heating cycle during which the shutdown criterion has been established.

30. The device according to claim 29, wherein said initialization unit comprises means for defining said initialization data in relation to said initialization data and data exchanged with said measurement and processing unit for said at least one of previous liquid bath.

31. The device according to claim 30, wherein said initialization unit is detachably connected to said measurement and processing unit.

32. The device according to claim 31 further comprising a detachable box, wherein said measurement and processing unit is fixed to said heating vat, and further wherein said initialization unit is disposed within said detachable box.

33. The device according to claim 32, wherein said heating vat is fitted with a plurality of resistors for heating said liquid bath, and further wherein said capacitive probe is disposed within said heating vat below said resistors.

34. The device according to claim 33, wherein said heating vat comprises a constant potential, and further wherein said capacitive probe comprises two electrodes whereby at least one of said two electrodes is at said constant potential of said heating vat.

* * * * *

UNITED STATES PATENT AND TRADEMARK OFFICE
CERTIFICATE OF CORRECTION

PATENT NO. : 6,600,306 B1
DATED : July 29, 2003
INVENTOR(S) : Pernot et al.

It is certified that error appears in the above-identified patent and that said Letters Patent is hereby corrected as shown below:

Drawings,
Sheet 6, Fig. 9, in the triangular-shaped box labeled "A" the "-" and "+" indicators should be reversed in location as follows:

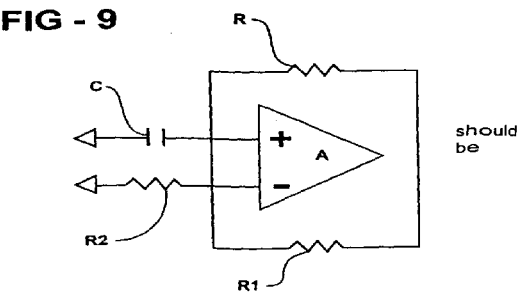 should be 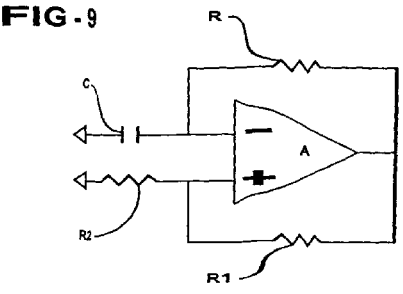

Column 3,
Line 19, "providing" should be replace with -- that provides --.

Signed and Sealed this

Thirty-first Day of August, 2004

JON W. DUDAS
*Director of the United States Patent and Trademark Office*

UNITED STATES PATENT AND TRADEMARK OFFICE
CERTIFICATE OF CORRECTION

PATENT NO. : 6,600,306 B1
DATED : July 29, 2003
INVENTOR(S) : Pernot et al.

It is certified that error appears in the above-identified patent and that said Letters Patent is hereby corrected as shown below:

Signed and Sealed this

Thirty-first Day of August, 2004

JON W. DUDAS
*Director of the United States Patent and Trademark Office*

UNITED STATES PATENT AND TRADEMARK OFFICE
CERTIFICATE OF CORRECTION

PATENT NO. : 6,600,306 B1
DATED : July 29, 2003
INVENTOR(S) : Pernot et al.

Page 1 of 1

It is certified that error appears in the above-identified patent and that said Letters Patent is hereby corrected as shown below:

Drawings,
Sheet 6, Fig. 9, in the triangular-shaped box labeled "A" the "-" and "+" indicators should be reversed in location as follows:

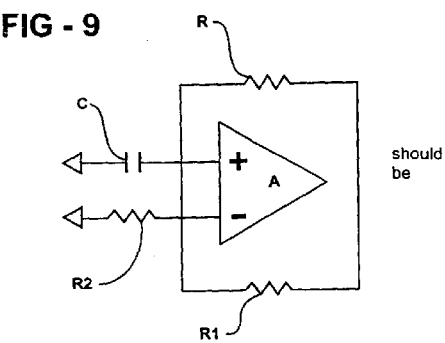 should be 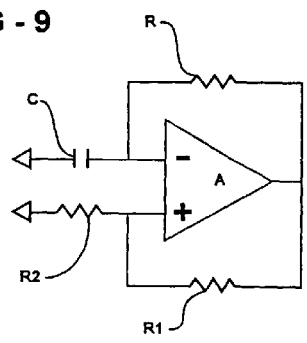

Column 3,
Line 19, "providing" should be replaced with -- that provides --.

Signed and Sealed this

Fourteenth Day of September, 2004

JON W. DUDAS
*Director of the United States Patent and Trademark Office*